United States Patent [19]

Adachi et al.

[11] Patent Number: 4,993,185

[45] Date of Patent: Feb. 19, 1991

[54] PROCESS FOR IMPROVING QUALITY OF FRUIT

[75] Inventors: Takashi Adachi; Takafumi Ishii; Hidemasa Hidaka, all of Kanagawa, Japan

[73] Assignee: Meiji Seika Kaisha, Ltd., Tokyo, Japan

[21] Appl. No.: 168,764

[22] Filed: Mar. 16, 1988

[30] Foreign Application Priority Data

Mar. 17, 1987 [JP] Japan .................................. 62-60061

[51] Int. Cl.$^5$ .............................................. A01G 7/06
[52] U.S. Cl. ...................................................... 47/58
[58] Field of Search .................... 47/1, 58, 1.4; 71/65, 71/77

[56] References Cited

U.S. PATENT DOCUMENTS

| | | | |
|---|---|---|---|
| 2,866,296 | 12/1958 | Meadows | 47/58 |
| 3,885,949 | 5/1975 | Ono | 71/79 |
| 4,125,392 | 11/1978 | Primo | 71/65 |
| 4,234,688 | 11/1980 | Righelato et al. | 435/101 |
| 4,490,467 | 12/1984 | Jarmon et al. | 435/101 |
| 4,599,233 | 7/1986 | Misato et al. | 424/127 |

*Primary Examiner*—James R. Feyrer
*Attorney, Agent, or Firm*—Sughrue, Mion, Zinn, Macpeak & Seas

[57] ABSTRACT

The quality including sugar content of fruit can be readily improved regardless of the climate or varieties by applying alginic oligosaccharide(s), which are obtained by enzymatically decomposing or hydrolyzing alginic acid, derivatives thereof or materials containing the same, to a fruit tree.

5 Claims, No Drawings

PROCESS FOR IMPROVING QUALITY OF FRUIT

BACKGROUND OF THE INVENTION

1. Field of the Invention

This invention relates to a process for improving the quality including sugar content of fruit which comprises applying alginic acid oligosaccharide(s) to a fruit tree in order to produce more delicious fruit.

2. Description of the Prior Art

The production and shipping of various fruits such as tangerine (Citrus Unshiu) in Japan amount to six million tons per year.

The deliciousness of fruit significantly varies among varieties. Therefore it has been vigorously attempted to improve fruit plants in order to produce highly delicious fruit. However, plant breeding requires a great deal of efforts and a prolonged period of time. Further, a fruit variety, which would exhibit a "deliciousness" under specific cultivation conditions including sunshine hours, photoperiod, atmospheric temperature and rainfall, would fail to exhibit the "deliciousness" unless it is grown under appropriate conditions. Thus it is difficult to produce "delicious" fruit on a nationwide scale in Japan where the climate shows considerable variations. The "deliciousness" of fruit would generally depend on the sugar content thereof. The necessary sugar content for each fruit has been determined through organoleptic tests. For example, the lower limit of the sugar content in fruit which are regarded as delicious is 11.0 for tangerine, 12.5 for apple, 16.0 for persimmon, 15.0 for grape, 11.0 for melon, 10.0 for orange, and 9.0 for grapefruit. The sugar content as used herein is expressed as a Brix degree measured with a sugar refractometer, with cane sugar being taken as a standard.

It can also be expected to enhance "deliciousness" by lowering the content of an organic acid such as citric acid.

SUMMARY OF THE INVENTION

Therefore, it is an object of the present invention to provide a process for improving the quality of fruit.

The present inventors have widely studied in order to find materials capable of increasing the sugar content of fruit regardless of the climate or varieties or of lowering the content of organic acids, and consequently found that a product obtained by decomposing alginic acid or alginic acid oligosaccharide(s), which are the main components of said decomposition product, would exert the aimed effect, thus completing the present invention.

According to the present invention there is provided a process for improving the quality of fruit which comprises applying alginic acid oligosaccharides to a fruit tree.

DETAILED DESCRIPTION OF THE INVENTION

The alginic acid oligosaccharides to be used in the present invention are defined as follows. Namely, they are oligosaccharide compositions obtained by decomposing alginic acid, sodium alginate, polyethylene glycol, alginate, algae containing alginic acid such as sea weed (*Laminaria japonica*), a microorganism-originated polysaccharide, etc., with an enzyme such has alginate lyase, or by hydrolyzing the above-described materials with an acid such as hydrochloric acid, or they are the main oligosaccharide components of the compositions. The main constituent saccharides of the oligosaccharides are guluronic acid and mannuronic acid. The composition of the alginic acid oligosaccharides comprises:

(1) oligosaccharides consisting of 2 to 20 molecules of guluronic acid only;
(2) oligosaccharides consisting of 2 to 20 molecules of mannuronic acid only;
(3) oligosaccharides consisting of 2 to 20 molecules in total of guluronic acid and mannuronic acid;
(4) a mixture of oligosaccharides (1) above and guluronic acid and/or mannuronic acid;
(5) a mixture of oligosaccharides (2) above and guluronic acid and/or mannuronic acid;
(6) a mixture of oligosaccharides (3) above and guluronic acid and/or mannuronic acid; or
(7) products obtained by heating to decompose compositions (b 1) to (6) above at a temperatuare of from 100 to 130° C. for 15 to 180 minutes at pH of from 1 to 4.

The composition described above is, for example, prepared as follows.

As alginic acid for use as the raw material, any alginic acid-containing raw materials, e.g., commercially available alginic acid or sodium alginate; algae containing alginic acid, such as Laminaria, Ecklomia cava, Lessonica, Durvilla; alginic acid-like polysaccharides produced by microorganisms such as Pseudomonas, can be utilized.

In the description, unless otherwise indicated, all parts and percents are by weight.

As a means for decomposing the alginic acid, a method of decomposing with an acid such as hydrochloric acid and sulfuric acid and a method of decomposing with an enzyme such as alginate lyase, can be applied. The hydrolysis of alginic acid with an acid may be carried out by, for example, adding 100 parts of water to five parts of sodium alginate, dissolving alginic acid in the water, adding three parts of a concentrated hydrochloric acid thereto; heating the resulting mixture to 90 to 100° C. for two to four hours, filtering the mixture, neutralizing the filtrate with caustic soda, and then concentrating the same to give the aimed alginic acid oligosaccharides. On the other hand, the decomposition of alginic acid with alginate lyase may be carried out by adding 100 parts of water to five parts of sodium alginate to dissolve alginic acid in the water, adjusting the pH value of the solution to the optimum level of the enzyme, adding 100 to 4,000 U of the enzyme per gram of the sodium alginate, and allowing the mixture to react at the optimum temperature of the enzyme for 24 to 48 hours to give the aimed alginic acid oligosaccharides.

When an abalone gastrointestinal enzyme (Abalone Acetone Powder ®; manufactured by Merck Co., Inc.) is employed as the alginate lyase, the optimum pH value of the enzyme is 7 to 8 and the optimum temperature thereof is 20 to 35° C.

The enzymatic activity of the alginate lyase is expressed by taking as one unit an enzymatic activity thereof capable of raising the absorbance of a 0.2% solution of sodium alginate at 230 nm by 0.01 at pH 7.0 and at a temperature of 30° C. in 30 minutes.

Alternatively, the oligosaccharides may be directly prepared from algae in the following manner. 1,300 parts of water is added to 40 parts of dry *Laminaria japonica* and the pH value of the mixture is adjusted to 11. The mixture is then ground with a homogenizer and treated at 60° C. for three hours. After adjusting the pH value to 5.5, 0.5%, on a solid basis, of cellulase (Meicellase; manufactured by Meiji Seika Kaisha, Ltd.) is added to the mixture. The mixture is then allowed to react at 40° C. for 20 hours. The pH value of the reaction mixture is adjusted to 7.0 and 1,000 U of alginate lyase per gram of the solid matter is added thereto. Thereafter, the mixture is further allowed to react at 30° C. for 48 hours. Thus the aimed alginic acid oligosaccharides is directly obtained from L. japonica.

The content of the alginic acid oligosaccharides in each decomposition product obtained above varies depending on the starting material. For example, a composition obtained by decomposing sodium alginate with an enzyme contains 40 to 100% of alginic oligosaccharides. On the other hand, that obtained from an alga such as L. japonica contains 10 to 25% thereof on a solid basis.

The alginic acid oligosaccharide(s) thus obtained are formulated into a solution of a concentration of 50 to 500 $\gamma$/ml, and 5 to 30 l of the obtained solution is sprayed onto a fruit tree such as a tangerine tree. Thus highly delicious fruit having an increased sugar content can be obtained. Also, the alginic acid oligosaccharide solution can be applied by soil treatment with it at the same concentration as above in amounts of 5–100 l per fruit tree.

The present invention is described in more detail by way of the following examples.

EXAMPLE 1

Sodium alginate was dissolved in water to give a 3% wt/vol solution. Alginate lyase (Abalone Acetone Powder) was added thereto at a ratio of 4,000 U per gram of alginic acid. The resulting mixture was allowed to react at a pH 7.0 and at 40° C. for 48 hours to thereby give oligosaccharides. After adjusting the pH value to 3.0, the reaction mixture was heated to 120° C. for two hours. Then the reaction mixture was neutralized to give a pH value of 7.0. The alginic acid oligosaccharides thus obtained was formulated into 10 $\gamma$/ml, 50 $\gamma$/ml, 200 $\gamma$/ml, 500 $\gamma$/ml and 1,000 $\gamma$/ml solutions. 10 l portions of each solution were sprayed onto the tangerine trees twice from the growth stage to the full-ripe stage. Tangerines were then harvested at random. The sugar content of each fruit was determined in a conventional manner and compared with that of control tangerines obtained from an untreated lot. Table 1 shows the results (n=20).

TABLE 1

| Alginic Aid Oligosaccharide Concentration ($\gamma$/ml) | Average Sugar Content* |
|---|---|
| 10 | 10.4 ± 0.77 |
| 50 | 11.2 ± 0.63 |
| 200 | 12.4 ± 0.82 |
| 500 | 12.3 ± 0.65 |
| 1,000 | 10.6 ± 0.71 |
| Control | 10.2 ± 0.85 |
|  | (n = 20) |

Note:
*This value is expressed as a Brix degree measured with a sugar refractometer, with cane sugar being taken as a standard.

From Table 1 it is apparent that the application of the alginic acid oligosaccharides at concentrations of 50 to 500 $\gamma$/ml significantly increased the sugar content of the fruit. In tangerines a sugar content of 11.0 or above is required for them to be evaluated as delicious. Thus the control tangerines of an average sugar content of 10.2 were unsatisfactory in sweetness. On the other hand, the tangerines obtained from the alginic acid oligosaccharides application lots (50 to 500 $\gamma$/ml) showed sufficient sugar contents of 11.2 to 12.4 and were ogranoleptically evaluated as delicious.

EXAMPLE 2

A medium comprising 0.5% of sodium alginate, 0.5% of peptone, 0.25% of yeast extract, 0.64% of $MgSO_4 \cdot 7H_2O$, 0.96% of NaCl and 20% of seawater, which will be called an LB medium hereinafter, was prepared. 30 ml portions of this medium were pipetted into 200-ml Erlenmeyer flasks and sterilized at 120° C. for 15 minutes. One platinum loopful of Alteromonas sp. LB 102 (FERM BP-1779) strain was then inoculated thereto and cultured therein at 240 rpm for 20 hours in order to obtain give a seed culture at 25° C.

3 l of the LB medium was introduced into a 5-l jar fermenter and sterilized at 120° C. for 15 minutes. Then 20 ml of the above-obtained seed culture was inoculated thereto and cultured therein at 240 rpm for 24 hours at 25° C. This culture medium was centrifuged at 10,000 rpm for 30 minutes. After removing the cells, the supernatant was purified with a hollow fiber through which only materials of a molecular weight of 10,000 or below could pass. Thus 250 ml of an enzyme solution showing an alginate lyase activity of 980 U/ml was obtained.

Next 240 g of Laminaria japonica was cut into pieces of 1 cm square. 4 l of a 1% $Na_2CO_3$ solution was added thereto and the mixture was heat-treated at 90° C. for one hour. Subsequently it was ground and neutralized by adding 2 l of a 2.2% HCl solution tehreto to give a pH value of 5.5. To the resulting solution, 1.8 g of a cellulase preparation (Meicellase; manufactured by Meiji Seika Kaisha, Ltd.) was added and the resulting mixture was allowed to react at 40° C. for six hours. After the completion of the reaction, the pH of the mixture was adjusted to 7.0, and 60,000 U of the alginate lyase obtained above was added thereto. The mixture thus obtained was allowed to react at 40° C. for 48 hours to give alginic acid oligosaccharides.

The alginic acid oligosaccharides thus obtained were dissolved to give a 200 $\gamma$/ml solution thereof. 10 l portions of this solution were applied by spraying onto the tangerine trees twice from the growth stage to the full-ripe stage. Tangerines were then harvested at random and the sugar content of each fruit was compared with that of control tangerines harvested from an untreated lot. Table 2 shows the results (n=20).

TABLE 2

| Lot | Sugar Content* |
|---|---|
| Test lot (applied with 200 $\gamma$/ml of alginic acid oligosaccharides) | 12.1 ± 0.68 |
| Control lot | 10.3 ± 0.77 |

Note:
*This value is expressed as a Brix degree measured with a sugar refractometer, with cane sugar being taken as a standard.

It is readily apparent from Table 2 that the sugar content of the tangerines obtained from the test lot to which alginic acid oligosaccharides were applied was higher than that of the control lot by approximately two points. Further, the former was highly evaluated in an organoleptic test.

EXAMPLE 3

The same procedures as in Example 1 wsere repeated except that the concentration of the alginic acid oligosaccharide solution sprayed was 500 $\gamma$/ml and the spraying was effected three times. The results are shown in Table 3 (n=20).

TABLE 3

| Lot | Sugar Content[*1] | Acid Content[*2] |
| --- | --- | --- |
| Test lot (applied with 500 $\gamma$/ml of alginic acid oligosaccharides) | 11.5 ± 0.65 | 0.85 ± 0.04 |
| Control lot | 10.3 ± 0.74 | 1.02 ± 0.05 |

Note:
[*1]This value is expressed as a Brix degree measured with a sugar refractometer, with cane sugar being taken as a standard.
[*2]This value is the number of grams of citric acid in 100 ml of fruit juice.

From the data in Table 3 it is readily apparent that spraying a 500 $\gamma$/ml solution of the alginic acid oligosaccharides increased the sugar content and decreased the acid content. Further, the tangerines obtained from the test lot was evaluated as delicious in an organoleptic test.

According to the present invention, the quality of fruit can be readily improved and thus delicious fruit can be produced, regardless of the climate, by applying alginic acid oligosaccharide(s) to fruit trees.

While the invention has been described in detail and with reference to specific embodiments thereof, it will be apparent to one skilled in the art that various changes and modifications can be made therein without departing from the spirit and scope thereof.

What is claimed is:

1. A process for improving the quality of fruit which comprises applying alginic acid oligosaccharide(s) to a fruit tree.

2. A process as in claim 1, wherein the alginic acid oligosaccharides are oligosaccharide compositions or main oligosaccharide components of said compositions which are obtained by decomposing alginic acid, sodium alginate, polyethylene glycol alginate, algae containing alginic acid, or polysaccharides originating from microorganisms, with an enzyme.

3. A process as in claim 1, wherein the alginic acid oligosaccharides are oligosaccharide compositions or main oligosaccharide components of said compositions which are obtained by hydrolyzing alginic acid, sodium alginate, polyethylene glycol alginate, algae containing alginic acid, or polysaccharides originating from microorganisms, with an acid.

4. A process as in claim 1, wherein the alginic acid oligosaccharides are applied to a fruit tree by spraying thereonto 5 to 30 l of a solution containing said alginic acid oligosaccharides at a concentration of 50 to 500 $\gamma$/ml.

5. A process as in claim 1, wherein the alginic acid oligosaccharides are applied to a fruit tree by soil treatment with 5 to 100 l of a solution containing said alginic acid oligosaccharides at a concentration of 50 to 500 $\gamma$/ml.

* * * * *